US00PP34522P2

(12) United States Plant Patent
van Langen

(10) Patent No.: US PP34,522 P2
(45) Date of Patent: Aug. 23, 2022

(54) ***ECHEVERIA* PLANT NAMED 'AMIECH2101'**

(50) Latin Name: ***((Echeveria pulidonis* E. Walther x *(Echeveria gibbiflora* x *Echeveria elegans))* x *Echeveria lilacina Kimnach)* x *Echeveria agavoides***
Varietal Denomination: 'AMIECH2101'

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 17/803,330

(22) Filed: May 14, 2022

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

(56) References Cited

PUBLICATIONS

Evergreenseeds website. 2022. *Echeveria* Black Prince: Caring for the Dramatic yet easy succulent. https://www.evergreenseeds.com/echeveria-black-prince/#:~:text=Echeveria%20Black%20Prince%20is%20a%20hybrid%2C%20evergreen%20succulent%20and%20its,a%20nursery%20in%20Capitola%2C%20California. 10 pages. (Year: 2022).*

* cited by examiner

*Primary Examiner* — Karen M Redden
(74) *Attorney, Agent, or Firm* — Samuel R. McCoy, Jr.

(57) ABSTRACT

A new and distinct *Echeveria* hybrid plant named 'AMIECH2101' which is characterized by a compact rosette of loosely held succulent foliage, greyed-green juvenile foliage at the center of the rosette which is lightly suffused with greyed-purple, foliage which becomes progressively darker greyed-green and progressively suffused with greyed-purple as it matures, light greyed-green foliar margins which become progressively suffused with greyed-red as the foliage matures, and the stability of these characteristics from generation to generation.

4 Drawing Sheets

Latin name of the genus and species: The Latin name of the genus and species of the novel variety disclosed herein is ((*Echeveria pulidonis* E. Walther x (*Echeveria gibbiflora* x *Echeveria elegans*)) x *Echeveria lilacina* Kimnach) x *Echeveria agavoides*.

Variety denomination: The inventive variety of *Echeveria* hybrid disclosed herein has been given the variety denomination 'AMIECH2101'.

BACKGROUND OF THE INVENTION

Parentage: 'AMIECH2101' is an interspecific hybrid seedling selection resulting from the controlled pollination of an unnamed (*Echeveria pulidonis* E. Walther x (*Echeveria gibbiflora* x *Echeveria elegans*)) x *Echeveria lilacina* Kimnach & R.C. Moran plant (not patented), the seed parent, with an unnamed *Echeveria agavoides* plant (not patented), the pollen parent. The crossing was made by the inventor in the spring of 2017 at a commercial greenhouse in Heerhugowaard, the Netherlands. In summer of 2018, one seedling was observed which exhibited unique growth and foliage characteristics. The seedling was isolated for further evaluation in order to confirm the distinctness and stability of the characteristics first observed. Upon confirmation of distinctness and stability, 'AMIECH2101' was selected for commercialization in autumn of 2018.

Asexual Reproduction: Asexual reproduction of the new cultivar 'AMIECH2101', by way of rooting leaf cuttings, was first initiated in the summer of 2019 at the inventor's commercial greenhouse in Heerhugowaard, the Netherlands. Through three subsequent generations, the unique features of this cultivar have proven to be stable and true to type.

SUMMARY OF THE INVENTION

The cultivar 'AMIECH2101' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH2101'. These characteristics in combination distinguish 'AMIECH2101' as a new and distinct *Echeveria* hybrid cultivar:

1. 'AMIECH2101' exhibits a compact rosette of somewhat loosely held foliage; and
2. 'AMIECH2101' exhibits thick, durable foliage; and
3. 'AMIECH2101' exhibits greyed-green juvenile foliage at the center of the rosette which is lightly suffused with greyed-purple; and
4. 'AMIECH2101' exhibits foliage which becomes progressively darker greyed-green and progressively suffused with greyed-purple as it matures, towards the outer whorls of the rosette; and
5. 'AMIECH2101' exhibits light greyed-green foliar margins which become progressively suffused with greyed-red as the foliage matures, towards the outer whorls of the rosette.

BOTANICAL DESCRIPTION OF THE PLANT

Figure 1:
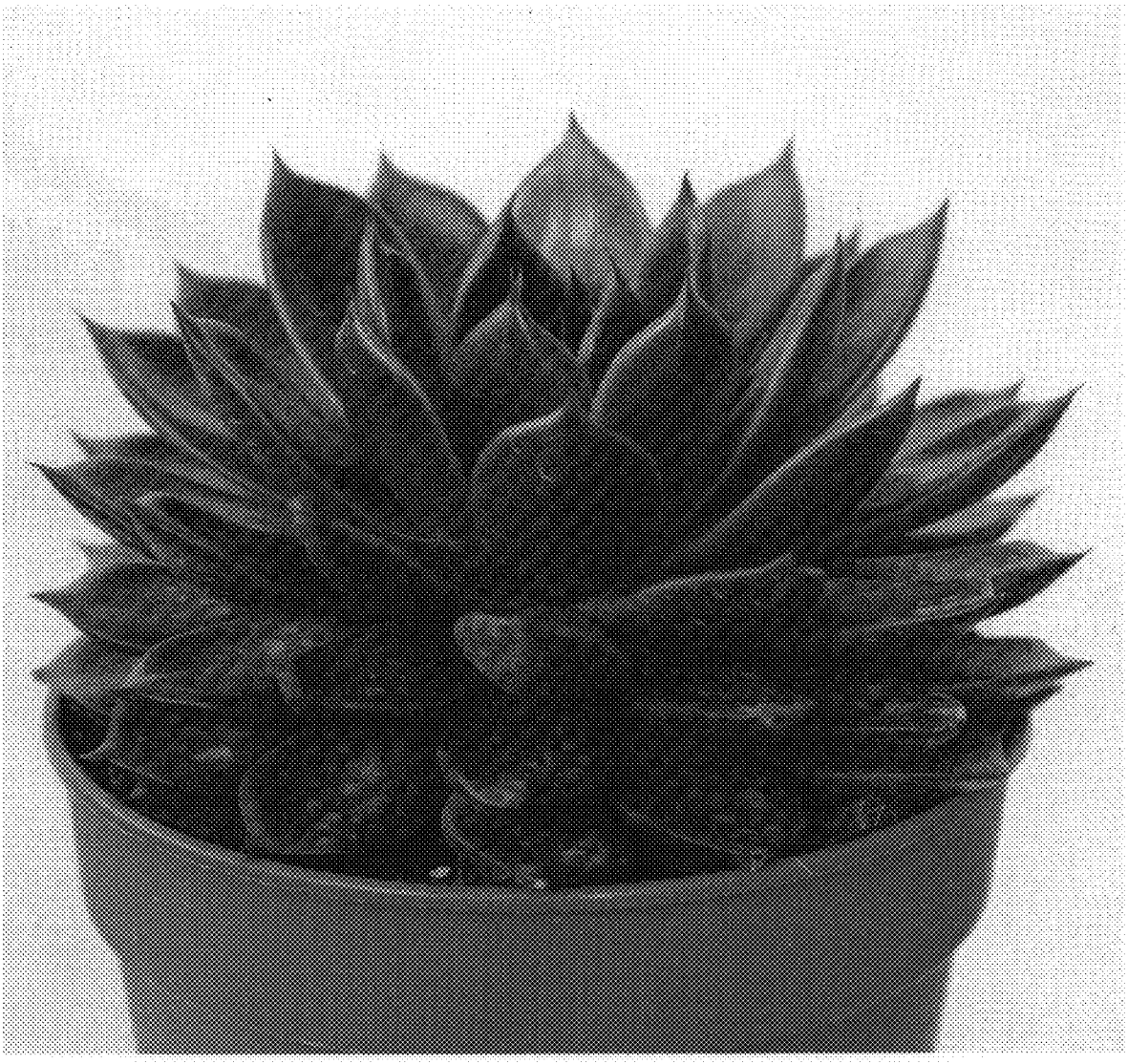
FIG. 1 illustrates, as nearly true as it is reasonably possible to make the same in color photographs of this type, an exemplary plant of 'AMIECH2101' grown in a commercial greenhouse in Heerhugowaard, the Netherlands. This plant is approximately 30 weeks old, shown planted in an 11.5 cm container.
Figure 2:
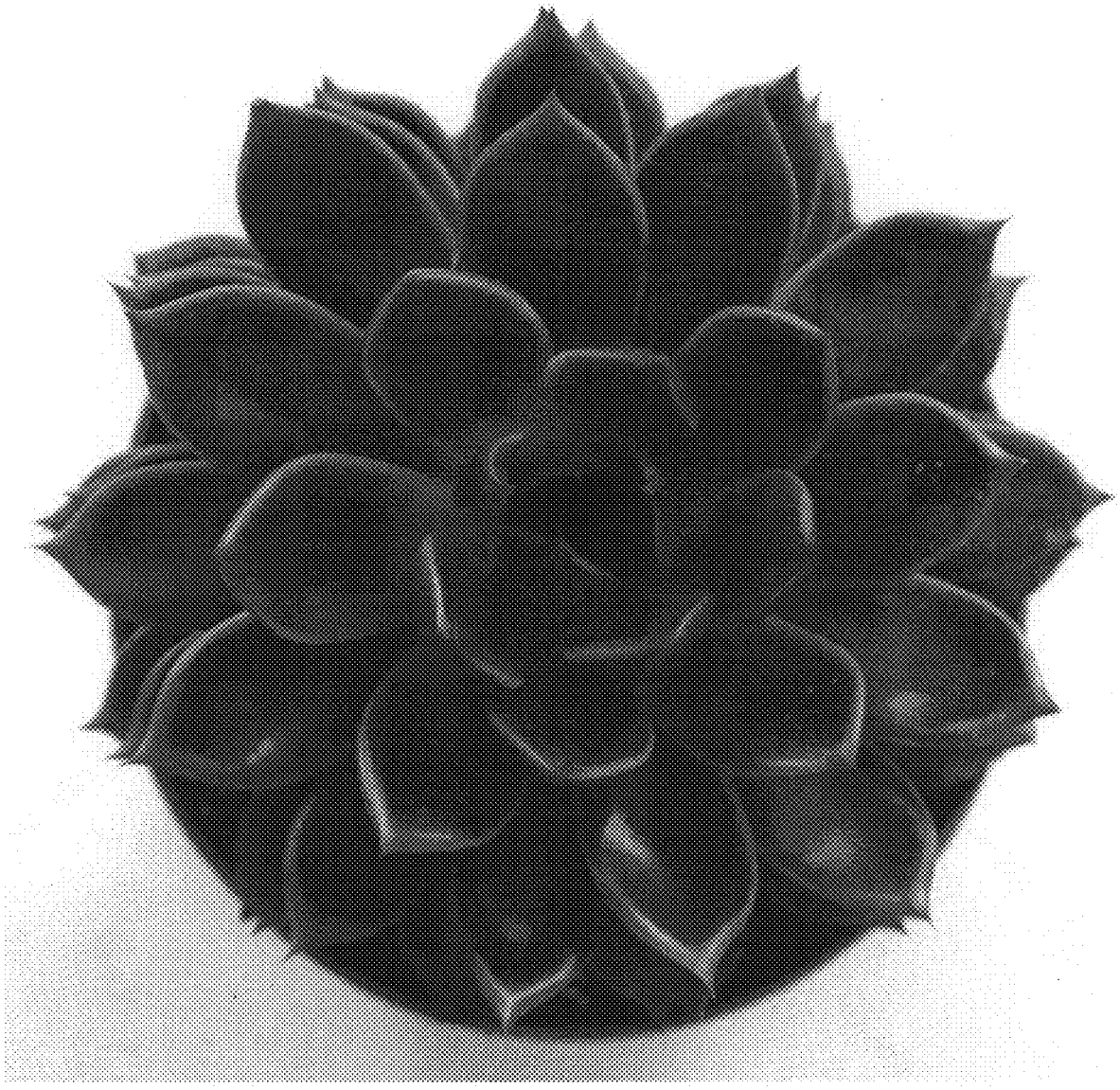
FIG. 2 illustrates, as nearly true as it is reasonably possible to make the same in color photographs of this type, the typical foliage arrangement of 'AMIECH2101'.
Figure 3:
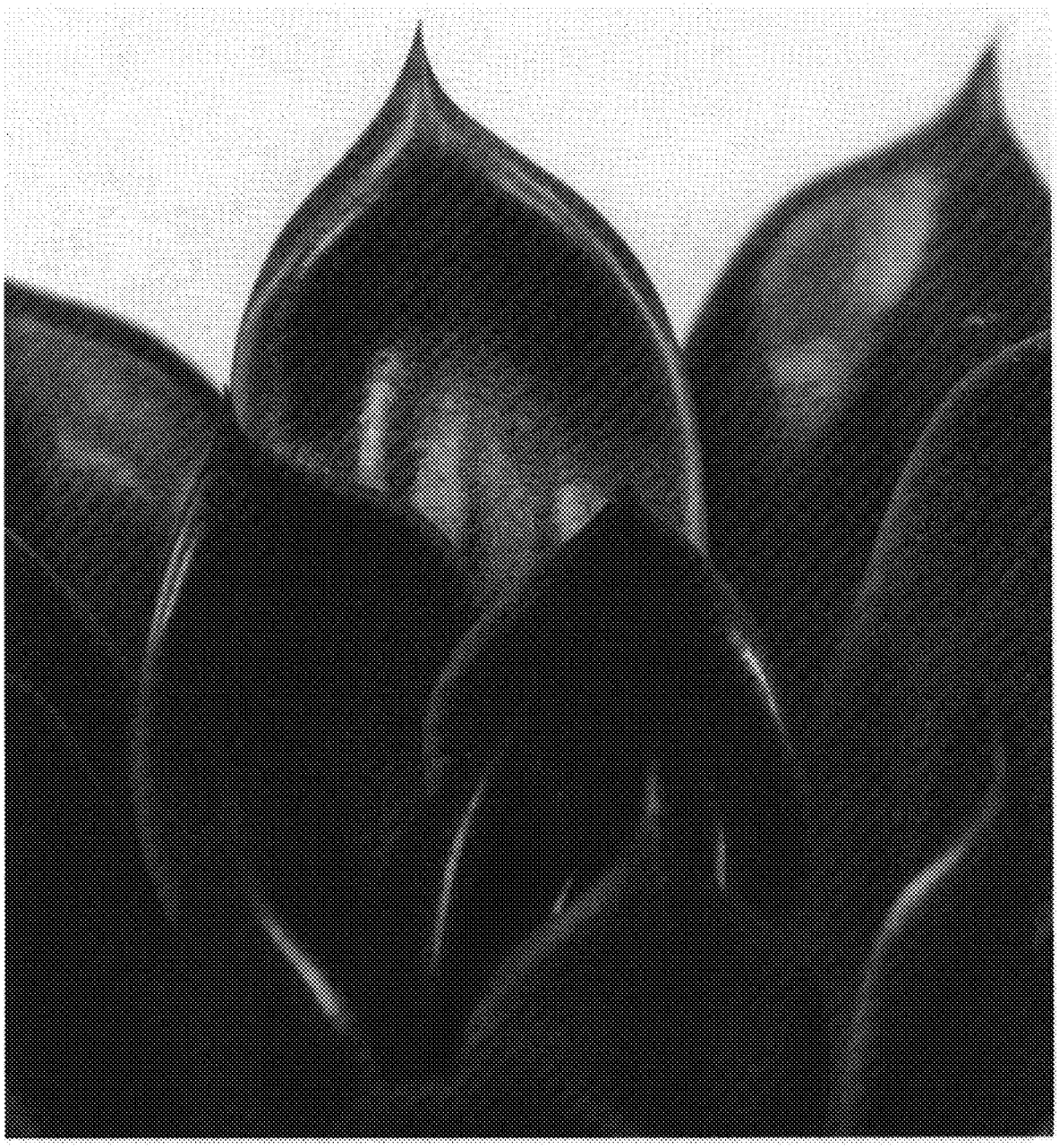
FIG. 3 illustrates, as nearly true as it is reasonably possible to make the same in color photographs of this type, the adaxial surface of the mature foliage 'AMIECH2101'.
Figure 4:
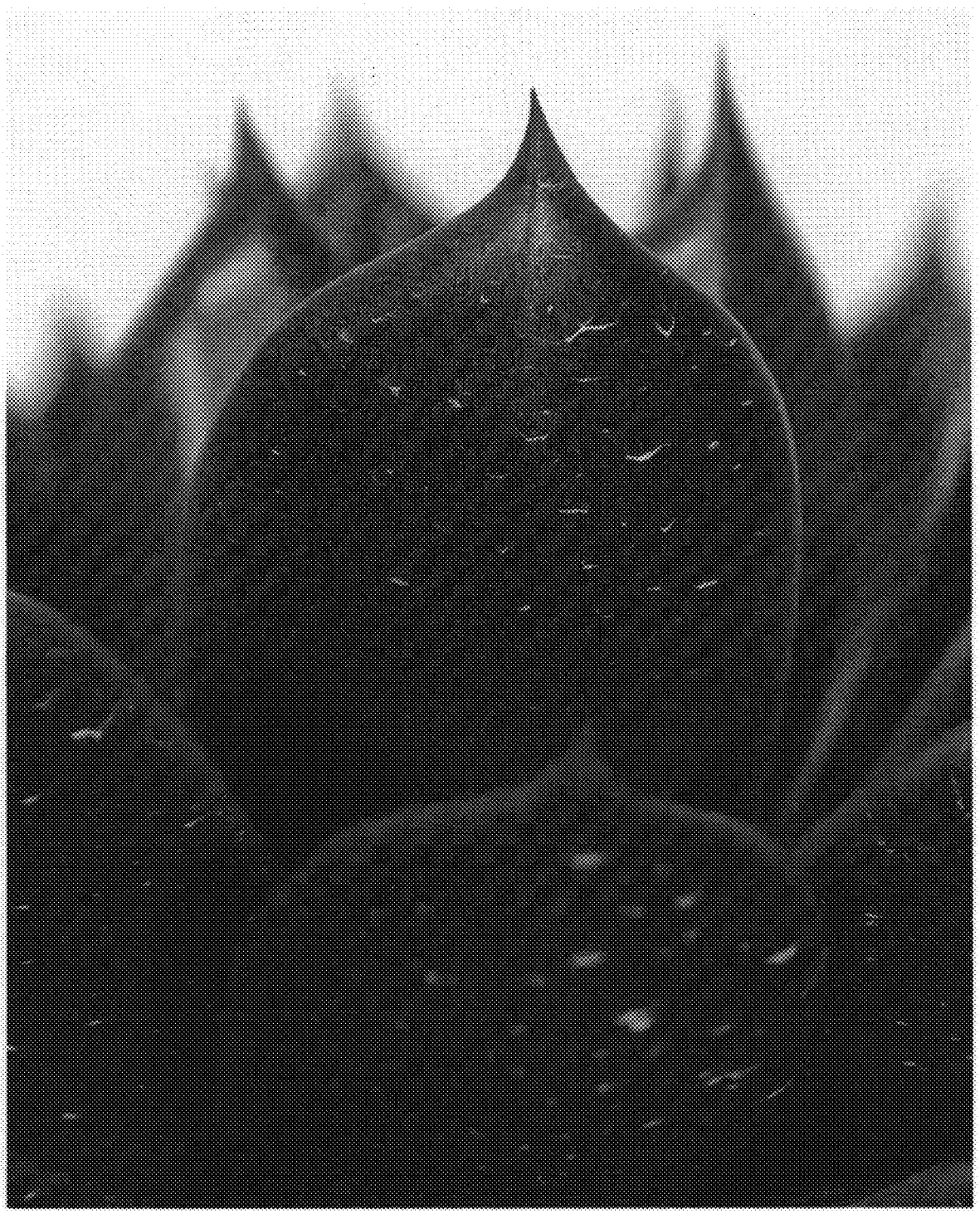
FIG. 4 illustrates, as nearly true as it is reasonably possible to make the same in color photographs of this type, the abaxial surface of the mature foliage 'AMIECH2101'.

The following observations and measurements made in February of 2022 describe averages from a sample set of six specimens of 30-week-old 'AMIECH2101' plants grown in 11.5 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and Botrytis as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH2101' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH2101' and comparisons with the parent plants and closest known comparator are provided below.

Plant description:

*Growth habit*.—Succulent perennial with foliage growing in a non-branched basal rosette.

*Plant shape*.—Flattened globular.

*Height from soil level to top of foliar plane*.—7.5 cm.

*Plant spread*.—Average of 13.2 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 35 weeks to produce a marketable plant in a 7 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosette; no main branches or lateral branches present.

Foliage:

*Arrangement*.—Rosette.

*Division*.—Simple.

*Attachment*.—Sessile.

*Quantity*.—Approximately 100 leaves per rosette.

*Shape*.—Obovate.

*Dimensions*.—5.8 cm long, 2.1 cm wide, and 0.8 cm thick, on average.

*Aspect*.—Very slightly concave and slightly curled upward, distally.

*Attitude*.—Juvenile foliage at the center of the rosette is held erect; foliage becomes progressively more relaxed towards the outer whorls of mature foliage which lay nearly horizontal.

*Apex*.—Broad apiculate.

*Base*.—Cuneate.

*Margin*.—Entire, with no undulation.

*Pubescence, texture and luster of the adaxial surface*.—Smooth, glabrous, and moderately glossy.

*Pubescence, texture and luster of the abaxial surface*.—Smooth, glabrous, and moderately glossy.

*Color*.—Juvenile foliage, adaxial surface — Nearest to a mixture of green and yellow-green, RHS NN137A and 147A; fading to yellow-green towards the base, RHS 147D; margins are greyed-green, nearest to RHS 194B, and become suffused with greyed-purple distally, nearest to RNS 183B. Juvenile foliage, abaxial surface — Yellow-green, nearest to a RHS 148B, and progressively suffused with greyed-purple towards the apex, nearest to RHS N186C; fading to greyed-green towards the base, nearest to a combination of RHS 196B and 196C; base is lightly suffused with white, N155C; apical margins are greyed-purple, nearest to a combination of RHS 183A and 183B. Mature foliage, adaxial surface — Nearest to a mixture of greyed-green to brown, RHS N189A and N200A, and suffused with greyed-purple nearest to RHS N186C; fading to greyed-green towards the base, nearest to RHS 194B; margined greyed-red, nearest to RHS 178A; tipped greyed-purple, nearest to RHS 184A. Mature foliage, abaxial surface — Brown, nearest to a mixture of RHS 200B and 200C, and suffused with greyed-purple, nearest to RHS N186C; fading to greyed-green towards the base, nearest to RHS 195A; margined greyed-red, nearest to RHS 178A; tipped greyed-purple, nearest to 184A. Venation, adaxial surface — No visible venation. Venation, abaxial surface — No visible venation.

*Petiole*.—No petiole; leaves are sessile.

Inflorescence: No flowering has been observed to date.

COMPARISONS WITH THE PARENT PLANTS AND CLOSEST KNOWN COMPARATOR

Plants of the new cultivar 'AMIECH2101' differ from the seed parent, an unnamed (*Echeveria pulidonis* E. Walther x (*Echeveria gibbiflora* x *Echeveria elegans*)) x *Echeveria lilacina* Kimnach & R.C. Moran plant (not patented), in the following characteristics described in Table 1 below.

TABLE 1

| Characteristic | 'AMIECH2101' | The seed parent. |
|---|---|---|
| Foliage shape. | Shorter and broader than the seed parent. | Longer and narrower than 'AMIECH2101'. |
| General coloration of the mature foliage. | Dark greyed-green and suffused with dark greyed-purple; margins are a bright greyed-red. | Light greyed-green. |

Plants of the new cultivar 'AMIECH2101' differ from the pollen parent, an unnamed *Echeveria agavoides* plant (not patented), in the following characteristics described in Table 2 below.

TABLE 2

| Characteristic | 'AMIECH2101' | The pollen parent. |
|---|---|---|
| General coloration of the mature foliage. | Dark greyed-green and suffused with dark greyed-purple; margins are a bright greyed-red. | Light yellow-green and lightly covered with a very thin layer of very light greyed-green epicuticular wax. |

COMPARISONS WITH THE CLOSEST KNOWN COMPARATOR

Plants of the new cultivar 'AMIECH2101' differ from the closest known commercial comparator, *Echeveria* hybrid 'AMIECH2102' (U.S. Plant application Ser. No. 17/803,332 filed concurrently), in the following characteristics described in Table 3 below.

TABLE 3

| Characteristic | 'AMIECH2101' | 'AMIECH2102' |
|---|---|---|
| Plant size. | Smaller than 'AMIECH2102'. | Larger than 'AMIECH2101'. |
| Foliage abundance. | More abundant than 'AMIECH2102'. | Less abundant than 'AMIECH2101'. |
| Foliage size. | Smaller than 'AMIECH2102'. | Larger than 'AMIECH2101'. |
| General coloration of the mature foliage. | A darker shade of greyed-green and more heavily suffused with greyed-purple. | A lighter shade of greyed-green with less greyed-purple suffusion, relative to 'AMIECH2101'. |

That which is claimed is:

1. A new and distinct variety of ((*Echeveria pulidonis* E. Walther x (*Echeveria gibbiflora* x *Echeveria elegans*)) x *Echeveria lilacina* Kimnach) x *Echeveria agavoides* plant named 'AMIECH2101', substantially as described and illustrated herein.

* * * * *